United States Patent [19]
Park et al.

[11] Patent Number: 5,543,320
[45] Date of Patent: Aug. 6, 1996

[54] ANTIBODIES TO INTERLEUKEN-7 RECEPTORS

[75] Inventors: Linda S. Park; Raymond G. Goodwin, both of Seattle, Wash.

[73] Assignee: Immunex Corporation, Seattle, Wash.

[21] Appl. No.: 83,243

[22] Filed: Jun. 25, 1993

Related U.S. Application Data

[62] Division of Ser. No. 907,366, Jul. 1, 1992, Pat. No. 5,264, 416, which is a division of Ser. No. 493,588, May 21, 1990, Pat. No. 5,194,375, which is a continuation-in-part of Ser. No. 421,201, Oct. 13, 1989, abandoned, which is a continuation-in-part of Ser. No. 366,910, Jun. 15, 1989, abandoned.

[51] Int. Cl.⁶ ............................. C12N 5/12; C07K 16/28; C12P 21/08

[52] U.S. Cl. ............................. 435/240.27; 530/388.23; 530/387.9

[58] Field of Search .................. 530/388.23, 387.9; 435/240.27

[56] References Cited

PUBLICATIONS

Waldmann Science vol. 252, 1647, 1991.
Harris et al. TibTech vol. 11 p. 42 1993.
Hird et al., Geves and Carver Ed. Sakora and Carney p. 181, 1990.

*Primary Examiner*—Lila Feisee
*Attorney, Agent, or Firm*—Kathryn A. Anderson; Scott G. Hallquist

[57] ABSTRACT

Mammalian Interleukin-7 receptor proteins, DNAs and expression vectors encoding mammalian IL-7 receptors, antibodies to mammalian Interleukin 7 receptors and processes for producing mammalian IL-7 receptors as products of recombinant cell culture, are disclosed.

6 Claims, 9 Drawing Sheets

FIGURE 2A

```
CTCTCTCTCTATCTCTCTCAGA                                                    22

ATG ACA ATT CTA GGT ACA ACT TTT GGC ATG GTT TTT TCT TTA CTT              67
Met Thr Ile Leu Gly Thr Thr Phe Gly Met Val Phe Ser Leu Leu              - 6
                              1
CAA GTC GTT TCT GGA GAA AGT GGC TAT GCT CAA AAT GGA GAC TTG              112
Gln Val Val Ser Gly Glu Ser Gly Tyr Ala Gln Asn Gly Asp Leu               10
                                         20
GAA GAT GCA GAA CTG GAT GAC TAC TCA TTC TCA TGC TAT AGC CAG              157
Glu Asp Ala Glu Leu Asp Asp Tyr Ser Phe Ser Cys Tyr Ser Gln               25
                    30                                       40
TTG GAA GTG AAT GGA TCG CAG CAC TCA CTG ACC TGT GCT TTT GAG              202
Leu Glu Val Asn Gly Ser Gln His Ser Leu Thr Cys Ala Phe Glu               40
                                    50
GAC CCA GAT GTC AAC ACC ACC AAT CTG GAA TTT GAA ATA TGT GGG              247
Asp Pro Asp Val Asn Thr Thr Asn Leu Glu Phe Glu Ile Cys Gly               55
                    60                                       70
GCC CTC GTG GAG GTA AAG TGC CTG AAT TTC AGG AAA CTA CAA GAG              292
Ala Leu Val Glu Val Lys Cys Leu Asn Phe Arg Lys Leu Gln Glu               70
                                    80
ATA TAT TTC ATC GAG ACA AAG AAA TTC TTA CTG ATT GGA AAG AGC              337
Ile Tyr Phe Ile Glu Thr Lys Lys Phe Leu Leu Ile Gly Lys Ser               85
                    90                                      100
AAT ATA TGT GTG AAG GTT GGA GAA AAG AGT CTA ACC TGC AAA AAA              382
Asn Ile Cys Val Lys Val Gly Glu Lys Ser Leu Thr Cys Lys Lys              100
                                   110
ATA GAC CTA ACC ACT ATA GTT AAA CCT GAG GCT CCT TTT GAC CTG              427
Ile Asp Leu Thr Thr Ile Val Lys Pro Glu Ala Pro Phe Asp Leu              115
                   120                                      130
AGT GTC ATC TAT CGG GAA GGA GCC AAT GAC TTT GTG GTG ACA TTT              472
Ser Val Ile Tyr Arg Glu Gly Ala Asn Asp Phe Val Val Thr Phe              130
                                   140
AAT ACA TCA CAC TTG CAA AAG AAG TAT GTA AAA GTT TTA ATG CAT              517
Asn Thr Ser His Leu Gln Lys Lys Tyr Val Lys Val Leu Met His              145
                   150                                      160
GAT GTA GCT TAC CGC CAG GAA AAG GAT GAA AAC AAA TGG ACG CAT              562
Asp Val Ala Tyr Arg Gln Glu Lys Asp Glu Asn Lys Trp Thr His              160
                                   170
GTG AAT TTA TCC AGC ACA AAG CTG ACA CTC CTG CAG AGA AAG CTC              607
Val Asn Leu Ser Ser Thr Lys Leu Thr Leu Leu Gln Arg Lys Leu              175
                   180                                      190
CAA CCG GCA GCA ATG TAT GAG ATT AAA GTT CGA TCC ATC CCT GAT              652
Gln Pro Ala Ala Met Tyr Glu Ile Lys Val Arg Ser Ile Pro Asp              190
```

FIGURE 2B

```
                            200
CAC TAT TTT AAA GGC TTC TGG AGT GAA TGG AGT CCA AGT TAT TAC    697
His Tyr Phe Lys Gly Phe Trp Ser Glu Trp Ser Pro Ser Tyr Tyr    205

210                                    220
TTC AGA ACT CCA GAG ATC AAT AAT AGC TCA GGG GAG ATG GAT CCT    742
Phe Arg Thr Pro Glu Ile Asn Asn Ser Ser Gly Glu Met Asp Pro    220

230
ATC TTA CTA ACC ATC AGC ATT TTG AGT TTT TTC TCT GTC GCT CTG    787
Ile Leu Leu Thr Ile Ser Ile Leu Ser Phe Phe Ser Val Ala Leu    235

240                                    250
TTG GTC ATC TTG GCC TGT GTG TTA TGG AAA AAA AGG ATT AAG CCT    832
Leu Val Ile Leu Ala Cys Val Leu Trp Lys Lys Arg Ile Lys Pro    250

260
ATC GTA TGG CCC AGT CTC CCC GAT CAT AAG AAG ACT CTG GAA CAT    877
Ile Val Trp Pro Ser Leu Pro Asp His Lys Lys Thr Leu Glu His    265

270                                    280
CTT TGT AAG AAA CCA AGA AAA AAT TTA AAT GTG AGT TTC AAT CCT    922
Leu Cys Lys Lys Pro Arg Lys Asn Leu Asn Val Ser Phe Asn Pro    280

290
GAA AGT TTC CTG GAC TGC CAG ATT CAT AGG GTG GAT GAC ATT CAA    967
Glu Ser Phe Leu Asp Cys Gln Ile His Arg Val Asp Asp Ile Gln    295

300                                    310
GCT AGA GAT GAA GTG GAA GGT TTT CTG CAA GAT ACG TTT CCT CAG    1012
Ala Arg Asp Glu Val Glu Gly Phe Leu Gln Asp Thr Phe Pro Gln    310

320
CAA CTA GAA GAA TCT GAG AAG CAG AGG CTT GGA GGG GAT GTG CAG    1057
Gln Leu Glu Glu Ser Glu Lys Gln Arg Leu Gly Gly Asp Val Gln    325

330                                    340
AGC CCC AAC TGC CCA TCT GAG GAT GTA GTC GTC ACT CCA GAA AGC    1102
Ser Pro Asn Cys Pro Ser Glu Asp Val Val Val Thr Pro Glu Ser    340

350
TTT GGA AGA GAT TCA TCC CTC ACA TGC CTG GCT GGG AAT GTC AGT    1147
Phe Gly Arg Asp Ser Ser Leu Thr Cys Leu Ala Gly Asn Val Ser    355

360                                    370
GCA TGT GAC GCC CCT ATT CTC TCC TCT TCC AGG TCC CTA GAC TGC    1192
Ala Cys Asp Ala Pro Ile Leu Ser Ser Ser Arg Ser Leu Asp Cys    370

380
AGG GAG AGT GGC AAG AAT GGG CCT CAT GTG TAC CAG GAC CTC CTG    1237
Arg Glu Ser Gly Lys Asn Gly Pro His Val Tyr Gln Asp Leu Leu    385

390                                    400
CTT AGC CTT GGG ACT ACA AAC AGC ACG CTG CCC CCT CCA TTT TCT    1282
Leu Ser Leu Gly Thr Thr Asn Ser Thr Leu Pro Pro Pro Phe Ser    400
```

FIGURE 2C

```
                                    410
CTC CAA TCT GGA ATC CTG ACA TTG AAC CCA GTT GCT CAG GGT CAG    1327
Leu Gln Ser Gly Ile Leu Thr Leu Asn Pro Val Ala Gln Gly Gln     415

420                                         430
CCC ATT CTT ACT TCC CTG GGA TCA AAT CAA GAA GAA GCA TAT GTC    1372
Pro Ile Leu Thr Ser Leu Gly Ser Asn Gln Glu Glu Ala Tyr Val     430

440
ACC ATG TCC AGC TTC TAC CAA AAC CAG TGA                        1402
Thr Met Ser Ser Phe Tyr Gln Asn Gln End                         439

AGTGTAAGAA ACCCAGACTG AACTTACCGT GAGCGACAAA GATGATTTAA          1452

AAGGGAAGTC TAGAGTTCCT AGTCTCCCTC ACAGCACAGA GAAGACAAAA          1502

TTAGCAAAAC CCCACTACAC AGTCTGCAAG ATTCTGAAAC ATTGCTTTGA          1552

CCACTCTTCC TGAGTTCAGT GGCACTCAAC ATGAGTCAAG AGCATCCTGC          1602

TTCTACCATG TGGATTTGGT CACAAGGTTT AAGGTGACCC AATGATTCAG          1652

CTATTTAAAA AAAAAAAAAA AA                                       1674
```

FIGURE 3A

```
CACATCTACT CTCTCTCTCT ATCTCTCTCA GA                                          32

ATG ACA ATT CTA GGT ACA ACT TTT GGC ATG GTT TTT TCT TTA CTT                  77
Met Thr Ile Leu Gly Thr Thr Phe Gly Met Val Phe Ser Leu Leu                  -6
                 1                                          10
CAA GTC GTT TCT GGA GAA AGT GGC TAT GCT CAA AAT GGA GAC TTG                 122
Gln Val Val Ser Gly Glu Ser Gly Tyr Ala Gln Asn Gly Asp Leu                  10
                                    20
GAA GAT GCA GAA CTG GAT GAC TAC TCA TTC TCA TGC TAT AGC CAG                 167
Glu Asp Ala Glu Leu Asp Asp Tyr Ser Phe Ser Cys Tyr Ser Gln                  25
                30                                      40
TTG GAA GTG AAT GGA TCG CAG CAC TCA CTG ACC TGT GCT TTT GAG                 212
Leu Glu Val Asn Gly Ser Gln His Ser Leu Thr Cys Ala Phe Glu                  40
                                50
GAC CCA GAT GTC AAC ACC ACC AAT CTG GAA TTT GAA ATA TGT GGG                 257
Asp Pro Asp Val Asn Ile Thr Asn Leu Glu Phe Glu Ile Cys Gly                  55
            60                                      70
GCC CTC GTG GAG GTA AAG TGC CTG AAT TTC AGG AAA CTA CAA GAG                 302
Ala Leu Val Glu Val Lys Cys Leu Asn Phe Arg Lys Leu Gln Glu                  70
                            80
ATA TAT TTC ATC GAG ACA AAG AAA TTC TTA CTG ATT GGA AAG AGC                 347
Ile Tyr Phe Ile Glu Thr Lys Lys Phe Leu Leu Ile Gly Lys Ser                  85
            90                                      100
AAT ATA TGT GTG AAG GTT GGA GAA AAG AGT CTA ACC TGC AAA AAA                 392
Asn Ile Cys Val Lys Val Gly Glu Lys Ser Leu Thr Cys Lys Lys                 100
                            110
ATA GAC CTA ACC ACT ATA GTT AAA CCT GAG GCT CCT TTT GAC CTG                 437
Ile Asp Leu Thr Thr Ile Val Lys Pro Glu Ala Pro Phe Asp Leu                 115
                120                                     130
AGT GTC ATC TAT CGG GAA GGA GCC AAT GAC TTT GTG GTG ACA TTT                 482
Ser Val Ile Tyr Arg Glu Gly Ala Asn Asp Phe Val Val Thr Phe                 130
                                140
AAT ACA TCA CAC TTG CAA AAG AAG TAT GTA AAA GTT TTA ATG CAT                 527
Asn Thr Ser His Leu Gln Lys Lys Tyr Val Lys Val Leu Met His                 145
                150                                     160
GAT GTA GCT TAC CGC CAG GAA AAG GAT GAA AAC AAA TGG ACG CAT                 572
Asp Val Ala Tyr Arg Gln Glu Lys Asp Glu Asn Lys Trp Thr His                 160
                                170
GTG AAT TTA TCC AGC ACA AAG CTG ACA CTC CTG CAG AGA AAG CTC                 617
Val Asn Leu Ser Ser Thr Lys Leu Thr Leu Leu Gln Arg Lys Leu                 175
                180                                     190
CAA CCG GCA GCA ATG TAT GAG ATT AAA GTT CGA TCC ATC CCT GAT                 662
Gln Pro Ala Ala Met Tyr Glu Ile Lys Val Arg Ser Ile Pro Asp                 190
```

FIGURE 3B

```
                                        200
CAC TAT TTT AAA GGC TTC TGG AGT GAA TGG AGT CCA AGT TAT TAC    707
His Tyr Phe Lys Gly Phe Trp Ser Glu Trp Ser Pro Ser Tyr Tyr    205
            210                                         220
TTC AGA ACT CCA GAG ATC AAT AAT AGC TCA GGA TTA AGC CTA TCG    752
Phe Arg Thr Pro Glu Ile Asn Asn Ser Ser Gly Leu Ser Leu Ser    220
                                230
TAT GGC CCA GTC TCC CCG ATC ATA AGA AGA CTC TGG AAC ATC TTT    797
Tyr Gly Pro Val Ser Pro Ile Ile Arg Arg Leu Trp Asn Ile Phe    235

GTA AGA AAC CAA GAA AAA ATT                                    818
Val Arg Asn Gln Glu Lys Ile                                    242

TAAATGTGAG TTTCAATCCT GAAAGTTTCC TGGACTGCCA GATTCATAGG         868

GTGGATGACA TTCAAGCTAG AGATGAAGTG GAAGGTTTTC TGCAAGATAC         918

GTTTCCTCAG CAACTAGAAG AATCTGAGAA GCAGAGGCTT GGAGGGGATG         968

TGCAGAGCCC CAACTGCCCA TCTGAGGATG TAGTCATCAC TCCAGAAAGC         1018

TTTGGAAGAG ATTCATCCCT CACATGCCTG GCTGGGAATG TCAGTGCATG         1068

TGACGCCCCT ATTCTCTCCT CTTCCAGGTC CCTAGACTGC AGGGAGAGTG         1118

GCAAGAATGG GCCTCATGTG TACCAGGACC TCCTGCTTAG CCTTGGGACT         1168

ACAAACAGCA CGCTGCCCCC TxCATTTTCT CTCCAATCTG GAATCCTGAC         1218

ATTGAACCCA GTTGCTCAGG GTCAGCCCAT TCTTACTTCC CTGGGATCAA         1268

ATCAAGAAGA AGCATATGTC ACCATGTCCA GCTTCTACCA AAACCAGTGA         1318

AGTGTAAGAA ACCCAGACTG AACTTACCGT GAGCGACAAA GATGATTTAA         1368

AAGGGAAGTC TAGAGTTCCT AGTCTCCCTC ACAGCACAGA GAAGACAAAA         1418

TTAGCAAAA                                                      1427
```

FIGURE 4A

```
TCTCTCTCTC TCTCTCTCTC TCTCTCTCTC TCTCTCTCTC TCTCAGA                  47

ATG ATG GCT CTG GGT AGA GCT TTC GCT ATA GTT TTC TGC TTA ATT          92
Met Met Ala Leu Gly Arg Ala Phe Ala Ile Val Phe Cys Leu Ile          -6
                  1                                        10
CAA GCT GTT TCT GGA GAA AGT GGA AAT GCC CAG GAT GGA GAC CTA         137
Gln Ala Val Ser Gly Glu Ser Gly Asn Ala Gln Asp Gly Asp Leu          10
                                           20
GAA GAT GCA GAC GCG GAC GAT CAC TCC TTC TGG TGC CAC AGC CAG         182
Glu Asp Ala Asp Ala Asp Asp His Ser Phe Trp Cys His Ser Gln          25
                  30                                       40
TTG GAA GTG GAT GGA AGT CAA CAT TTA TTG ACT TGT GCT TTT AAT         227
Leu Glu Val Asp Gly Ser Gln His Leu Leu Thr Cys Ala Phe Asn          40
                                           50
GAC TCA GAC ATC AAC ACA GCT AAT CTG GAA TTT CAA ATA TGT GGG         272
Asp Ser Asp Ile Asn Thr Ala Asn Leu Glu Phe Gln Ile Cys Gly          55
                  60                                       70
GCT CTT TTA CGA GTG AAA TGC CTA ACT CTT AAC AAG CTG CAA GAT         317
Ala Leu Leu Arg Val Lys Cys Leu Thr Leu Asn Lys Leu Gln Asp          70
                                           80
ATA TAT TTT ATA AAG ACA TCA GAA TTC TTA CTG ATT GGT AGC AGC         362
Ile Tyr Phe Ile Lys Thr Ser Glu Phe Leu Leu Ile Gly Ser Ser          85
                  90                                      100
AAT ATA TGT GTG AAG CTT GGA CAA AAG AAT TTA ACT TGC AAA AAT         407
Asn Ile Cys Val Lys Leu Gly Gln Lys Asn Leu Thr Cys Lys Asn         100
                                          110
ATG GCT ATA AAC ACA ATA GTT AAA GCC GAG GCT CCC TCT GAC CTG         452
Met Ala Ile Asn Thr Ile Val Lys Ala Glu Ala Pro Ser Asp Leu         115
                 120                                      130
AAA GTC GTT TAT CGC AAA GAA GCA AAT GAT TTT TTG GTG ACA TTT         497
Lys Val Val Tyr Arg Lys Glu Ala Asn Asp Phe Leu Val Thr Phe         130
                                          140
AAT GCA CCT CAC TTG AAA AAG AAA TAT TTA AAA AAA GTA AAG CAT         542
Asn Ala Pro His Leu Lys Lys Lys Tyr Leu Lys Lys Val Lys His         145
                 150                                      160
GAT GTG GCC TAC CGC CCA GCA AGG GGT GAA AGC AAC TGG ACG CAT         587
Asp Val Ala Tyr Arg Pro Ala Arg Gly Glu Ser Asn Trp Thr His         160
                                          170
GTA TCT TTA TTC CAC ACA AGA ACA ACA ATC CCA CAG AGA AAA CTA         632
Val Ser Leu Phe His Thr Arg Thr Thr Ile Pro Gln Arg Lys Leu         175
                 180                                      190
CGA CCA AAA GCA ATG TAT GAA ATC AAA GTC CGA TCC ATT CCC CAT         677
Arg Pro Lys Ala Met Tyr Glu Ile Lys Val Arg Ser Ile Pro His         190
```

FIGURE 4B

```
                                    200
AAC GAT TAC TTC AAA GGC TTC TGG AGC GAG TGG AGT CCA AGT TCT  722
Asn Asp Tyr Phe Lys Gly Leu Trp Ser Glu Trp Ser Pro Ser Ser  205

210                             220
ACC TTC GAA ACT CCA GAA CCC AAG AAT CAA GGA GGA TGG GAT CCT  767
Thr Phe Glu Thr Pro Glu Pro Lys Asn Gln Gly Gly Trp Asp Pro  220

230
GTC TTG CCA AGT GTC ACC ATT CTG AGT TTG TTC TCT GTG TTT TTG  812
Val Leu Pro Ser Val Thr Ile Leu Ser Leu Phe Ser Val Phe Leu  235

240                             250
TTG GTC ATC TTA GCC CAT GTG CTA TGG AAA AAA AGG ATT AAA CCT  857
Leu Val Ile Leu Ala His Val Leu Trp Lys Lys Arg Ile Lys Pro  250

260
GTC GTA TGG CCT AGT CTC CCC GAT CAT AAG AAA ACT CTG GAA CAA  902
Val Val Trp Pro Ser Leu Pro Asp His Lys Lys Thr Leu Glu Gln  265

270                             280
CTA TGT AAG AAG CCA AAA ACG AGT CTG AAT GTG AGT TTC ATT CCC  947
Leu Cys Lys Lys Pro Lys Thr Ser Leu Asn Val Ser Phe Ile Pro  280

290
GAA ATT TTC CTG GAC TGC CAG ATT CAT GAG GTG AAA GGC GTT GAA  992
Glu Ile Phe Leu Asp Cys Gln Ile His Glu Val Lys Gly Val Glu  295

300                             310
GCC AGG GAC GAG GTG GAA ATT TTT CTG CCC AAT GAT CTT CCT GCA 1037
Ala Arg Asp Glu Val Glu Ile Phe Leu Pro Asn Asp Leu Pro Ala  310

320
CAG CCA GAG GAG TTG GAG ACA CAG GGA CAC AGA GCC GCT GTA CAC 1082
Gln Pro Glu Glu Leu Glu Thr Gln Gly His Arg Ala Ala Val His  325

330                             340
AGT GCA AAC CGC TCG CCT GAG ACT TCA GTC AGC CCA CCA GAA ACA 1127
Ser Ala Asn Arg Ser Pro Glu Thr Ser Val Ser Pro Pro Glu Thr  340

350
GTT AGA AGA GAG TCA CCT TTA AGA TGC CTG GCT AGA AAT CTG AGT 1172
Val Arg Arg Glu Ser Pro Leu Arg Cys Leu Ala Arg Asn Leu Ser  355

360                             370
ACC TGC AAT GCC CCT CCA CTC CTT TCC TCT AGG TCC CCT GAC TAC 1217
Thr Cys Asn Ala Pro Pro Leu Leu Ser Ser Arg Ser Pro Asp Tyr  370

380
AGA GAT GGT GAC AGA AAT AGG CCT CCT GTG TAT CAA GAC TTG CTG 1262
Arg Asp Gly Asp Arg Asn Arg Pro Pro Val Tyr Gln Asp Leu Leu  385

390                             400
CCA AAC TCT GGA AAC ACA AAT GTC CCT GTC CCT GTC CCT CAA CCA 1307
Pro Asn Ser Gly Asn Thr Asn Val Pro Val Pro Val Pro Gln Pro  400
```

FIGURE 4C

```
                                410
TTG CCT TTC CAG TCG GGA ATC CTG ATA CCA TTT TCT CAG AGA CAG    1352
Leu Pro Phe Gln Ser Gly Ile Leu Ile Pro Phe Ser Gln Arg Gln     415
            420                                         430
CCC ATC TCC ACT TCC TCA GTA CTG AAT CAA GAA GAA GCG TAT GTC    1397
Pro Ile Ser Thr Ser Ser Val Leu Asn Gln Glu Glu Ala Tyr Val     430
                            440
ACC ATG TCT AGT TTT TAC CAA AAC AAA TGA                        1427
Thr Met Ser Ser Phe Tyr Gln Asn Lys End                         439

ATTATAAGAA AACCCTTCCA TCGACAACCA AATGATCACT GAGATGGAAA         1477

GTCTGGAATG CTTGCTCTCC CCCGTAGCTC ACAGAAGAGA AAGTCAACGT         1527

GACCTTGCTA CACATCTCAG CATCTAACAA ATCATTTGCT CTTCTAGCTA         1577

GAAGCATTGC ACAAAGCAGG AAGAATCTGT TTTCCCTGTT GTTGGGTTAG         1627

TCATAAGAGT CCATATGACC CATTAAAATT GCAAAGCTCA GTTAAGTGAA         1677

GAAAGAAAGA TAGACAAAAG AAGATAGAAG GATGTGGTGA ATGCAGGAAG         1727

AAGAAAATGA AAGATGTGAG TGGTGGGTCT ATCATTCAAA TTGACTATTT         1777

ATCCAGCACT ATACCACTCT TCTCATTTCT TCCTCACAAT AATATTACAA         1827

TGTGGGCTTA TCCATTATAA CTTTTATTTT CTTTGTCATA GATGCTGAAG         1877

TTGAAAGTAG AGATTTTAAG TGATATCCAA ATTTTTCTTT CAGCTACAGA         1927

TGAGGCACAC ATTCCAACTT CAACCCTCTC TTGCCATGAA CCTGTCCTAT         1977

TGTTGAGTGT CAAACATCAC CACTAAGTGG ATGGTTATGT AGTCCATTAT         2027

CCAAACTGAG TCGTTTTGGA AAGAAAAAGT TAGACATAAT TAACAGTAAG         2077

CATAAATGTA TATGTCTAAG AGAGATGTGG ATGGATGGTC ATTTTACTTA         2127

AAGTGGCTAT AGGGATGAAC ATGAAGGACA AAGTACATTT ATGGGTGTGG         2177

CATACCATGA CCATGTGTCA AAGGAAGTGG GAAAAGAAA AAAAAAGCAC          2227

CAAGATCATT TGATTTTGTT TTGTTGTTTT GTTGAAAAC AAACTCAAGA          2277

AGCAATGAGT TAGAAGCCGA GAAGTTCCAG AGTCAGTTAT CAAGACCATG         2327

ATTTTCCTGC TGCTATTATC CATTGGCTTC TCTGTGACAT TGTAGGAGGA         2377

ACTATGGCCA ATCTACAGGA GTTCAACATT TAACAGTGAA TGGAGTCCTC         2427

CTATGTGAGT CCTCCTATGT GTGGAGACAC CATTAAGAA                    2466
```

5,543,320

1

ANTIBODIES TO INTERLEUKEN-7 RECEPTORS

CROSS-REFERENCE TO RELATED APPLICATION

This application is a divisional of U.S. Ser. No. 07/907,366, filed Jul. 1, 1992, issued as U.S. Pat. No. 5,264,416, which is a divisional of U.S. Ser. No. 07/493,588, filed May 21, 1990 and issued as U.S. Pat. No. 5,194,375, which is a continuation-in-part of U.S. Ser. No. 07/421,201, filed Oct. 13, 1989, which is a continuation-in-part of U.S. Ser. No. 07/366,910, filed Jun. 15, 1989, now abandoned.

BACKGROUND OF THE INVENTION

The present invention relates generally to cytokine receptors, and more specifically, to Interleukin-7 receptors.

Interleukin-7 (IL-7, also known as pre-B cell growth factor and lymphopoietin-1) is a mammalian endogenous secretory protein which is capable of inducing proliferation of bone marrow-derived lymphocyte progenitors and precursors, including the specialized precursors known as pre-B cells. IL-7 is also believed to be capable of stimulating other cell types, such as T cells and megakaryocytes; however, the full repertoire of cells capable of responding to IL-7 is not yet known. It is likely that IL-7 acts on a variety of cell types. Complementary DNA clones encoding IL-7 have recently been isolated (Goodwin et al., *Proc. Natl. Acad. Sci. USA* 86:302, 1989; Namen et al., *Nature* 333:571, 1988), permitting further structural and biological characterization of IL-7.

IL-7 initiates its biological effect on cells by binding to a specific IL-7 receptor protein expressed on the plasma membrane of an IL-7-responsive cell. Because of the ability of IL-7 to specifically bind IL-7 receptor (IL-7R), purified IL-7R compositions will be useful in diagnostic assays for IL-7, as well as in raising antibodies to IL-7 receptor for use in diagnosis and therapy. In addition, purified IL-7 receptor compositions may be used directly in therapy to bind or scavenge IL-7, thereby providing a means for regulating the immune activities of this cytokine. In order to study the structural and biological characteristics of IL-7R and the role played by IL-7R in the responses of various cell populations to IL-7 or other cytokine stimulation, or to use IL-7R effectively in therapy, diagnosis, or assay, purified compositions of IL-7R are needed. Such compositions, however, are obtainable in practical yields only by cloning and expressing genes encoding the receptors using recombinant DNA technology. Efforts to purify the IL-7R molecule for use in biochemical analysis or to clone and express mammalian genes encoding IL-7R have been impeded by lack of a suitable source of receptor protein or mRNA. Prior to the present invention, no cell lines were known to express high levels of IL-7R constitutively and continuously, which precluded purification of receptor for sequencing or construction of genetic libraries for direct expression cloning.

SUMMARY OF THE INVENTION

The present invention provides DNA sequences encoding mammalian Interleukin-7 receptors (IL-7R) or subunits thereof. Preferably, such DNA sequences are selected from the group consisting of (a) cDNA clones having a nucleotide sequence derived from the coding region of a native IL-7R gene; (b) DNA sequences which are capable of hybridization to the cDNA clones of (a) under moderately stringent conditions and which encode biologically active IL-7R molecules; and (c) DNA sequences which are degenerate as a result of the genetic code to the DNA sequences defined in (a) and. (b) and which encode biologically active IL-7R molecules. The present invention also provides recombinant expression vectors comprising the DNA sequences defined above, recombinant IL-7R molecules produced using the recombinant expression vectors, and processes for producing the recombinant IL-7R molecules using the expression vectors.

The present invention also provides substantially homogeneous or purified protein compositions comprising mammalian IL-7R. Preferred IL-7R proteins are soluble forms of the native receptors. Soluble receptors are truncated proteins wherein regions of the receptor molecule not required for IL-7 binding have been deleted.

The present invention also provides compositions for use in therapy, diagnosis, assay of IL-7R, or in raising antibodies to IL-7R, comprising effective quantities of soluble native or recombinant receptor proteins prepared according to the foregoing processes. These and other aspects of the present invention will become evident upon reference to the following detailed description and attached drawings.

BRIEF DESCRIPTION OF THE DRAWINGS

FIGS. 2A–2C depict the cDNA sequence and derived amino acid sequence of the human IL-7R clone H20. Nucleotides are numbered from the beginning of the 5' untranslated region. Amino acids are numbered from the beginning of the signal peptide sequence. The putative signal peptide sequence is represented by the amino acids at positions −20 through −1. The glutamic acid residue constituting the putative N-terminus of the mature sequence is underlined at position 1 of the protein sequence; the putative transmembrane region at amino acids 220–244 is also underlined.

FIGS. 3A–3B depict the cDNA sequence and derived amino acid sequence of human IL-7R clone H6. Clone H6 is an alternative RNA splicing construct which is believed to encode a native soluble IL-7R protein. Nucleotides and amino acids are numbered and identified as in FIGS. 2A–2C.

FIGS. 4A–4C depict the cDNA sequence and derived amino acid sequence of a hybrid murine IL-7R clone derived from murine clones P1 and P2 as described in Example 4. Nucleotides and amino acids are numbered and identified as in FIGS. 2A–2C and 3A–3B.

DETAILED DESCRIPTION OF THE INVENTION

Definitions

Figure 1:
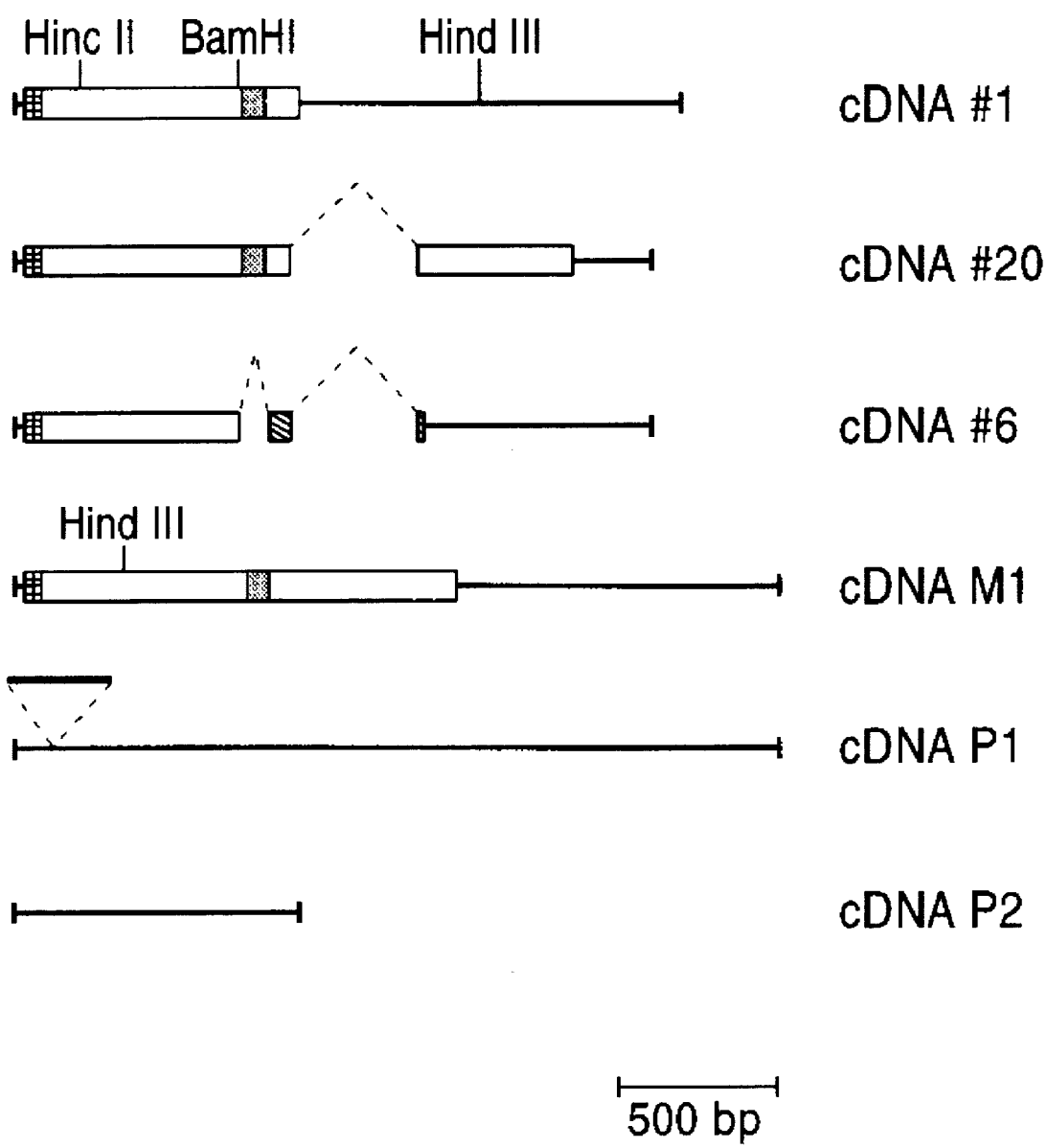
FIG. 1 shows restriction maps of cDNA clones containing regions encoding all or part of human and murine IL-7R proteins.

As used herein, the terms "IL-7 receptor" and "IL-7R" refer to proteins having amino acid sequences which are substantially similar to the native mammalian Interleukin-7 receptor amino acid sequences disclosed in FIGS. 2–4, and which are biologically active, as defined below, in that they are capable of binding Interleukin-7 (IL-7) molecules or transducing a biological signal initiated by an IL-7 molecule binding to a cell, or cross-reacting with anti-IL-7R antibodies raised against IL-7R from natural (i.e., nonrecombinant) sources. The terms "IL-7 receptor" or "IL-7R" include, but are not limited to, analogs or subunits of native proteins having at least 20 amino acids and which exhibit at least some biological activity in common with IL-7R. The calculated molecular weight of mature human IL-7R is 49,500. As used throughout the specification, the term "mature"

means a protein expressed in a form lacking a leader sequence as may be present in full-length transcripts of a native gene. Various bioequivalent protein and amino acid analogs are described in detail below.

The term "substantially similar," when used to define either amino acid or nucleic acid sequences, means that a particular subject sequence, for example, a mutant sequence, varies from a reference sequence by one or more substitutions, deletions, or additions, the net effect of which is to retain biological activity of the IL-7R protein. Alternatively, nucleic acid subunits and analogs are "substantially similar" to the specific DNA sequences disclosed herein if: (a) the DNA sequence is derived from the coding region of a native mammalian IL-7R gone; (b) the DNA sequence is capable of hybridization to DNA sequences of (a) under moderately stringent conditions and which encode biologically active IL-7R molecules; or DNA sequences which are degenerate as a result of the genetic code to the DNA sequences defined in (a) or (b) and which encode biologically active IL-7R molecules. Substantially similar analog proteins will be greater than about 30 percent similar to the corresponding sequence of the native IL-7R. Sequences having lesser degrees of similarity but comparable biological activity are considered to be equivalents. More preferably, the analog proteins will be greater than about 80 percent similar to the corresponding sequence of the native IL-7R, in which case they are defined as being "substantially identical." In defining nucleic acid sequences, all subject nucleic acid sequences capable of encoding substantially similar amino acid sequences are considered substantially similar to a reference nucleic acid sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Bid.* 48:443, 1970), as revised by Smith and Waterman (*Adv. Appl. Math.* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, ed., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps.

"Soluble IL-7 receptor" or "sIL7-R" as used in the context of the present invention refers to a protein, or a substantially equivalent analog, having an amino acid sequence corresponding to the extracellular region of native IL-7 receptors, for example, polypeptides having the amino acid sequences substantially equivalent to the sequences of amino acid residues 1–219 depicted in FIGS. 2A–2B, amino acid residues 1–242 depicted in FIGS. 3A– 3B, and amino acid residues 1–219 depicted in FIGS. 4A–4B. Equivalent sIL-7Rs include polypeptides which vary from the sequences shown in FIGS. 2–4 by one or more substitutions, deletions, or additions, and which retain the ability to bind IL-7 and inhibit the ability of IL-7 to transduce a signal via cell surface bound IL-7 receptor proteins. Because sIL- 7R proteins are devoid of a transmembrane region, they are secreted from the host cell in which they are produced. When administered in therapeutic formulations, sIL-7R proteins circulate in the body and bind to circulating IL-7 molecules, preventing interaction of IL-7 with natural IL- 7 receptors and inhibiting IL-7 dependent immune responses. The ability of a polypeptide to inhibit IL-7 signal transduction can be determined by transfecting cells with recombinant IL-7 receptor DNAs to obtain recombinant receptor expression. The cells are then contacted with IL-7 and the resulting metabolic effects examined. If an effect results which is attributable to the action of the ligand, then the recombinant receptor has signal transducing activity. Exemplary procedures for determining whether a polypeptide has signal transducing activity are disclosed by Idzerda et al., *J. Exp. Med.* March 1990, in press, Curtis et al., *Proc. Natl. Acad. Sci USA* 86:3045 (1989), Prywes et al., *EMBO J.* 5:2179 (1986) and Chou et al., *J. Biol. Chem.* 262:1842 (1987). Alternatively, primary cells or cell lines which express an endogenous IL-7 receptor and have a detectable biological response to IL-7 could also be utilized. For example, the IL-7 dependent cell line IxN/2b responds by short term proliferation in response to IL-7 and the IL-7 induced proliferation may be blocked specifically by the addition of exogenous soluble IL-7R.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli,* will be free of glycan. Protein expressed in yeast may have a glycosylation pattern different from that expressed in mammalian cells.

"Biologically active," as used throughout the specification as a characteristic of IL-7 receptors, means that a particular molecule shares sufficient amino acid sequence similarity with the embodiments of the present invention disclosed herein to be capable of binding detectable quantities of IL-7, transmitting an IL-7 stimulus to a cell, for example, as a component of a hybrid receptor construct, or cross-reacting with anti-IL-7R antibodies raised against IL-7R from natural (i.e., nonrecombinant) sources. Preferably, biologically active IL-7 receptors within the scope of the present invention are capable of binding greater than 0.1 nmoles IL-7 per nmole receptor, and most preferably, greater than 0.5 nmole IL-7 per nmole receptor in standard binding assays (see below).

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard .biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention can be assembled from eDNA fragments and short oligonucleotide linkers, or from a series of oligonucleotides, to provide a synthetic gene which is capable of being expressed in a recombinant transcriptional unit.

"Recombinant expression vector" refers to a replicable DNA construct used either to amplify or to express DNA which encodes IL-7R and which includes a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Isolation of cDNAs encoding IL-7R

In order to obtain the coding sequence of a mammalian IL-7R, a cDNA sequence encoding IL-7R can be isolated from a recombinant DNA library generated using either genomic DNA or cDNA. In a preferred approach, a cDNA library is constructed from polyadenylated mRNA obtained from a particular cell line which expresses a mammalian IL-7R. For example, the cDNA library can be constructed from the human fibroblast cell line WI-26VA4 (ATCC CCL 95.1) or the human Daudi cell line (ATCC CCL 213). Murine cell lines which express IL-7R may also be used, including the T-cell line LBRM-33-1A5 (ATCC CRL 8079), the pre-B cell line 70Z/3 (ATCC TIB 158), and the murine myelomonocytic cell line PU5-1.8 (ATCC TIB 61).

IL-7R sequences contained in the cDNA library can be readily identified by screening the library with an appropriate nucleic acid probe which is capable of hybridizing with IL-7R cDNA. The probe can incorporate nucleotide sequences disclosed herein. Alternatively, DNAs encoding IL-7R proteins can be assembled by ligation of synthetic oligonucleotide subunits to provide a complete coding sequence.

In making this invention, cDNAs encoding IL-7R were isolated by direct expression. A cDNA library was constructed by first isolating cytoplasmic mRNA from the human fibroblast cell line WI-26VA4. Polyadenylated RNA was isolated and used to prepare double-stranded cDNA. Purified cDNA fragments were then ligated into pDC302 vector DNA which uses regulatory sequences derived from pDC201 (a derivative of pMLSV, previously described by Cosman et al., *Nature* 312:768, 1984), SV40 and cytomegalovirus DNA, described in detail below in Example 2. pDC302 has been deposited with the American Type Culture Collection under the name pCAV/NOT-IL-7R (with an insert containing IL-7R clone H1) and assigned deposit accession number ATCC 68014. The pDC302 vectors containing the IL-7R cDNA fragments were transformed into *E. coli* strain DH5α. Transformants were plated to provide approximately 1,000 colonies per plate. The resulting colonies were harvested and each pool used to prepare plasmid DNA for transfection into COS-7 cells essentially as described by Cosman et al. (*Nature* 312:768, 1984) and Luthman et al. (*Nucl. Acid Res.* 11:1295, 1983). Transfectants expressing biologically active cell surface IL-7 receptors were identified by screening for their ability to bind $^{125}$I-IL-7. In this screening approach, transfected COS-7 cells were incubated with medium containing $^{125}$I-IL-7, the cells washed to remove unbound labeled IL-7, and the cell monolayers contacted with X-ray film to detect concentrations of IL-7 binding, as disclosed by Sims et al, *Science* 241:585 (1988). Transfectants detected in this manner appear as dark foci against a relatively light background.

Using this approach, approximately 100,000 cDNAs were screened in pools of approximately 1000 cDNAs until assay of one transfectant pool indicated positive loci for IL-7 binding. A frozen stock of bacteria from this positive pool was grown in culture and plated to provide individual colonies, which were screened until a single clone (clone H1) was identified which directed synthesis of a surface protein with detectable IL-7 binding activity. This clone was isolated, and its insert sequenced to determine the nucleotide sequence of the human IL-7R cDNA. The sequence of human IL-7R cDNA clone H1 isolated according to this method was then used as a hybridization probe to isolate human cDNA clone H20 (FIGS. 2A–2C), clone H6 (FIGS. 3A–3B), and murine clones P1 and P2 (a hybrid cDNA of which is shown in FIGS. 4A–4C) from appropriate libraries. Using analogous methods, cDNA clones can be isolated from cDNA libraries of other mammalian species by cross-species hybridization. For use in hybridization, DNA encoding IL-7R may be covalently labeled with a detectable substance such as a fluorescent group, a radioactive atom or a chemiluminescent group by methods well known to those skilled in the art. Such probes could also be used for in vitro diagnosis of particular conditions.

Like most mammalian genes, mammalian IL-7 receptors are presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Proteins and Analogs

The present invention provides substantially homogeneous recombinant mammalian IL- 7R polypeptides substantially free of contaminating endogenous materials and, optionally, without associated native-pattern glycosylation. Mammalian IL-7R of the present invention includes, by way of example, primate, human, murine, canine, feline, bovine, ovine, equine and porcine IL-7R. Derivatives of IL-7R within the scope of the invention also include various structural forms of the primary protein which retain biological activity. Due to the presence of ionizable amino and carboxyl groups, for example, an IL-7R protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to IL-7R amino acid side chains or at the N- or C-termini. Other derivatives of IL-7R within the scope of this invention include covalent or aggregative conjugates of IL-7R or its fragments with other proteins or polypeptides, such as by synthesis in recombinant culture as N-terminal or C-terminal fusions. For example, the conjugated peptide may be a a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). IL-7R protein fusions can comprise peptides added to facilitate purification or identification of IL-7R (e.g., poly-His). The amino acid sequence of IL-7 receptor can also be linked to the peptide Asp-Tyr-Lys-Asp-Asp-Asp-Asp-Lys (DYKDDDDK) (Hopp et al., *Bio/Technology* 6: 1204,1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*.

IL-7R derivatives may also be used as immunogens, reagents in receptor-based immunoassays, or as binding agents for affinity purification procedures of IL-7 or other binding ligands. IL-7R derivatives may also be obtained by cross-linking agents, such as M-maleimidobenzoyl succinimide ester and N-hydroxysuccinimide, at cysteine and lysine residues. IL-7R proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, IL-7R may be used to selectively bind (for purposes of assay or purification) anti-IL-7R antibodies or IL-7.

The present invention also includes IL-7R with or without associated native-pattern glycosylation. IL-7R expressed in yeast or mammalian expression systems, e.g., COS-7 cells, may be similar or slightly different in molecular weight and glycosylation pattern than the native molecules, depending upon the expression system. Expression of IL-7R DNAs in bacteria such as *E. coli* provides non-glycosylated molecules. Functional mutant analogs of mammalian IL-7R having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where A1 is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

IL-7R derivatives may also be obtained by mutations of IL-7R or its subunits. An IL-7R mutant, as referred to herein, is a polypeptide homologous to IL-7R but which has an amino acid sequence different from native IL-7R because of a deletion, insertion or substitution.

Bioequivalent analogs of IL-7R proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. In addition, differences in the several cDNA clones isolated from various cell lines indicate that amino acid 46 (relative to cDNA clone H20) may be Ile or Thr, amino acid 118 may be Val or Ile, amino acid 224 may be Thr or Ile and amino acid 336 may be Ile or Val. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered.

Subunits of IL-7R may be constructed by deleting terminal or internal residues or sequences. Particularly preferred subunits include those in which the transmembrane region and intracellular domain of IL-7R are deleted or substituted with hydrophilic residues to facilitate secretion of the receptor into the cell culture medium. The resulting protein is a soluble truncated IL-7R molecule which may retain its ability to bind IL-7. Particular examples of soluble IL-7R include polypeptides having substantial identity to the sequence of amino acid residues 1–219 in FIGS. 2A–2B, residues 1–242 in FIGS. 3A–3B, and residues 1–219 in FIGS. 4A–4B.

Mutations in nucleotide sequences constructed for expression of analog IL-7Rs must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed IL-7R mutants screened for the desired activity.

Not all mutations in the nucleotide sequence which encodes IL-7R will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques, January* 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Expression of Recombinant IL-7R

The present invention provides recombinant expression vectors which include synthetic or cDNA-derived DNA fragments encoding mammalian IL-7R or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

DNA sequences encoding mammalian IL-7 receptors which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence; exemplary DNA embodiments are those corresponding to the nucleotide sequences shown in the Figures. Other embodiments include sequences capable of hybridizing to the sequences of the Figures under moderately stringent conditions (50° C., 2 X SSC) and other sequences hybridizing or degenerate to those described above, which encode biologically active IL-7 receptor polypeptides.

Transformed host cells are cells which have been transformed or transfected with IL-7R vectors constructed using recombinant DNA techniques. Transformed host cells ordinarily express IL-7R, but host cells transformed for purposes of cloning or amplifying IL-7R DNA do not need to express IL-7R. Expressed IL-7R will be deposited in the cell membrane or secreted into the culture supernatant, depending on the IL-7R DNA selected. Suitable host cells for expression of mammalian IL-7R include prokaryotes, yeast or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed to produce mammalian IL-7R using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, New York, 1985), the relevant disclosure of which is hereby incorporated by reference.

Prokaryotic expression hosts may be used for expression of IL-7Rs that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include E. coli, Bacillus subtilis, Salmonella typhimurium, and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. E. coli is typically transformed using derivatives of pBR322, a plasmid derived from an E. coli species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage $\lambda$ $P_L$ promoter and cI857ts thermolabile repressor. Plasmid vectors available from the American Type Culture Collection which incorporate derivatives of the $\lambda$ $P_L$ promoter include plasmid pHUB2, resident in E. coli strain JMB9 (ATCC 37092) and pPLc28, resident in E. coli RR1 (ATCC 53082).

Recombinant IL-7R proteins may also be expressed in yeast hosts, preferably from the Saccharomyces species, such as S. cerevisiae. Yeast of other genera, such as Pichia or Ktuyveromyces may also be employed. Yeast vectors will generally contain an origin of replication from the 2μ yeast plasmid or an autonomously replicating sequence (ARS), promoter, DNA encoding IL-7R, sequences for polyadenylation and transcription termination and a selection gene. Preferably, yeast vectors will include an origin of replication and selectable marker permitting transformation of both yeast and E. coli, e.g., the ampicillin resistance gene of E. coli and S. cerevisiae trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et at., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et at., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Bid. Chem.* 258:2674, 1982) and Beier et al. (*Nature* 300:724, 1982). The yeast co-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 µg/ml adenine and 20 µg/ml uracil. Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 vital genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 vital origin of replication (Fiers et al., *Nature* 273:113, 1978). Smaller or larger SV40 fragments may also be used, provided the approximately 250 bp sequence extending from the Hind III site toward the BgtI site located in the vital origin of replication is included. Further, mammalian genomic IL-7R promoter, control and/ or signal sequences may be utilized, provided such control sequences are compatible with the host cell chosen. Additional details regarding the use of a mammalian high expression vector to produce a recombinant mammalian IL-7 receptor are provided in Example 2 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (Mol. Immunol. 23:935, 1986).

A particularly preferred eukaryotic vector for expression of IL-7R DNA is disclosed below in Example 2. This vector, referred to as pDC302, was derived from the mammalian high expression vector pDC201 and contains regulatory sequences from SV40, adenovirus-2, and human cytomegalovirus.

Purified mammalian IL-7 receptors or analogs are prepared by culturing suitable host/vector systems to express the recombinant translation products of the DNAs of the present invention, which are then purified from culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise an IL-7 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify an IL-7R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian IL-7R can be disrupted by any convenient method, including freeze-thaw cycling, sonication, mechanical disruption, or use of cell lysing agents.

Fermentation of yeast which express mammalian IL-7R as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Human IL-7R synthesized in recombinant culture is characterized by the presence of non-human cell components, including proteins, in amounts and of a character which depend upon the purification steps taken to recover human IL-7R from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of IL-7R free of proteins which may be normally associated with IL-7R as it is found in nature in its species of origin, e.g. in cells, cell exudates or body fluids.

IL-7R compositions are prepared for administration by mixing IL-7R having the desired degree of purity with physiologically acceptable carriers. Such carders will be nontoxic to recipients at the dosages and concentrations employed. Ordinarily, the preparation of such compositions entails combining the IL-7R with buffers, antioxidants such as ascorbic acid, low molecular weight (less than about 10 residues) polypeptides, proteins, amine acids, carbohydrates including glucose, sucrose or dextrins, chelating agents such as EDTA, glutathione and other stabilizers and excipients.

IL-7R compositions may be used to attenuate IL-7-mediated immune responses. To achieve this result, a therapeutically effective quantity of an IL-7 receptor composition is administered to a mammal, preferably a human, in association with a pharmaceutical carrier or diluent.

The following examples are offered by way of illustration, and not by way of limitation.

EXAMPLES

Example 1

Binding Assays

A. Radiolabeling of IL-7. Recombinant murine IL-7 was expressed in HeLa cells and purified substantially as described by Namen et al., *Nature* 333:571, 1988. The purified protein was radiolabeled using a commercially available enzymebead radioiodination reagent (BioRad). In this procedure 7.5 µg recombinant IL-7 in 50 µl 0.2M sodium phosphate, pH 7.2 were combined with 50 µl enzymebead reagent, 2 MCi of sodium iodide in 20 µl of 0.05 M sodium phosphate pH 7 and 10 µl of 2.5% β-D-glucose. After 10 min at 25° C., sodium azide (10 µl of 50 mM) and sodium metabisulfite (10 µl of 5 mg/ml) were added and incubation continued for 5 minutes at 25° C. The reaction mixture was fractionated by gel filtration on a 2 ml bed volume of Sephadex G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-IL-7 was diluted to a working stock solution of $1 \times 10^{-7}$M in binding medium and stored for up to one month at 4° C. without detectable loss of receptor binding activity. The specific activity is routinely in the range of $1-5 \times 10^{15}$ cpm/mmole IL-7.

B. Binding to Intact Cells. Binding assays done with cells grown in suspension culture or removed from culture flasks by treatment with EDTA (i.e., WI-26VA4) were performed by a phthalate oil separation method (Dower et at., *J. Immunol.* 132:751, 1984) essentially as described by Park et at., *J. Biol. Chem.* 261:4177, 1986. Binding assays were also done on COS cells transfected with a mammalian expression vector containing cDNA encoding either a human or murine IL-7R molecule. For Scatchard analysis of binding to intact cells, COS cells were transfected with plasmid DNA by the method of Luthman et al., *Nucl. Acids. Res.* 11:1295, 1983, and McCutchan et al., *J. Natn. Cancer Inst.* 41:351, 1968. Eight hours following transfection, cells were trypsinized, and reseeded in Costar six well plates at a density of $6 \times 10^4$ COS-IL-7 receptor transfectants/well mixed with $6 \times 10^5$ COS control transfected cells as carriers. Two days later monolayers were assayed for $^{125}$I-IL-7 binding either at 4° C. for two hours or 37° C. for 30 minutes essentially by the method described by Park et al., *J. Exp. Med.* 166:476, 1987. Nonspecific binding of $^{125}$I-IL-7 was measured in the presence of a 200-fold or greater molar excess of unlabeled IL-7. Sodium azide (0.2%) was included in ail binding assays to inhibit internalization of $^{125}$I-IL-7 by cells at 37° C.

C. Solid Phase Binding Assays. The ability of IL-7R to be stably adsorbed to nitrocellulose from detergent extracts of human or murine cells yet retain IL-7-binding activity provided a means of detecting IL-7R. Cell extracts were prepared by mixing a cell pellet with a 2 X volume of PBS containing 1% Triton X-100 and a cocktail of protease inhibitors (2 mM phenylmethyl sulfonyl fluoride, 10 µM pepstatin, 10 µM leupeptin, 2 mM o-phenanthroline and 2 mM EGTA) by vigorous vortexing. The mixture was incubated on ice for 10 minutes after which it was centrifuged at 12,000 x g for 10 minutes at 8° C. to remove nuclei and other debris. Two microliter aliquots of cell extracts were placed on dry BA85/21 nitrocellulose membranes (Schleicher and Schuell, Keene, N.H.) and allowed to dry. The membranes were incubated in tissue culture dishes for 30 minutes in Tris (0.05M) buffered saline (0.15M) pH 7.5 containing 3% w/v BSA to block nonspecific binding sites. The membrane was then covered with $5 \times 10^{-11}$M $^{125}$I-IL-7 in PBS+3% BSA and incubated for 2 hr at 4° C. with shaking. At the end of this time, the membranes were washed 3 times in PBS, dried and placed on Kodak X-Omat AR film for 18 hr at −70° C.

D. Binding Assay for Soluble IL-7R. Soluble IL-7R present in COS-7 cell supernatants was measured by inhibition of $^{125}$I-IL-7 binding to an IL-7-dependent cell line, such as IxN/2b (Namen et al., *J. Exp. Med.* 167:988, 1988; Park et al., *J. Exp. Med.* in press, 1990), or any other murine or human cell line expressing IL-7 receptors. Supernatants were harvested from COS-7 cells 3 days after transfection, concentrated 10-fold, and preincubated with $^{125}$I-IL-7 for 1 hour at 37° C. IxN/2b cells ($2 \times 10^6$) were added to a final volume of 150 ul, incubation continued for 30 minutes at 37° C., and binding was assayed and analyzed as described by Park et al., *J. Biol. Chem.* 261:4177, 1986.

Example 2

Isolation of Human IL-7 R cDNA by Direct Expression of Active Protein in COS-7 Cells Various murine and human cell lines were screened for expression of IL-7R based on their ability to bind $^{125}$I-labeled IL-7. The human fibroblast cell line Wl-26VA4 was found to express the highest number of receptors per cell of any cell lines tested. Equilibrium binding studies conducted according to Example 1B showed that the cell line exhibited biphasic binding of $^{125}$I-IL-7 with approximately 6,000 high affinity sites ($K_a=10^9-10^{10}$ $M^{-1}$) and 300,00 low affinity sites ($K_a=10^7-10^8$ $M^{-1}$) per cell.

A sized cDNA library was constructed by reverse transcription of polyadenylated mRNA isolated from total RNA extracted from human fibroblast WI-26VA4 cells grown in the presence of pokeweed mitogen using standard techniques (Gubler, et at., *Gene* 25:263, 1983; Ausubel et al., eds., *Current Protocols in Molecular Biology*, Vol. 1, 1987). The cells were harvested by lysing the cells in a guanidine hydrochloride solution and total RNA isolated as previously described (March et al., *Nature* 315:64 1, 1985).

Poly A$^+$ RNA was isolated by oligo dT cellulose chromatography and double-stranded cDNA was prepared by a method similar to that of Gubler and Hoffman (*Gene* 25:263, 1983). Briefly, the poly A$^+$ RNA was converted to an RNA-cDNA hybrid by reverse transcriptase using oligo dT as a primer. The RNA-cDNA hybrid was then converted into double-stranded cDNA using RNAase H in combination with DNA polymerase I. The resulting double stranded cDNA was blunt-ended with T4 DNA polymerase. To the blunt-ended cDNA is added EcoRI linker-adapters (having internal NotI sites) which were phosphorylated on only one end (Invitrogen). The linker-adaptered cDNA was treated with T4 polynucleotide kinase to phosphorylate the 5' overhanging region of the linker-adapter and unligated linkers were removed by running the cDNA over a Sepharose CL4B column. The linker-adaptered cDNA was ligated to an equimolar concentration of EcoRI cut and dephosphorylated arms of bacteriophage λgt10 (Huynh et al, *DNA Cloning: A Practical Approach*, Glover, ed., IRL Press, pp. 49–78). The ligated DNA was packaged into phage particles using a commercially available kit to generate a library of recombinants (Stratagene Cloning Systems, San Diego, Calif., USA). Recombinants were further amplified by plating phage on a bacterial lawn of *E. coli* strain c600(hfl⁻).

Phage DNA was purified from the resulting λgt10 cDNA library and the cDNA inserts excised by digestion with the restriction enzyme NotI. Following electrophoresis of the digest through an agarose gel, cDNAs greater than 500 bp were isolated.

The resulting cDNAs were ligated into the eukaryotic expression vector pDC302, which was designed to express cDNA sequences inserted at its multiple cloning site when transfected into mammalian cells. pDC302 was assembled from pDC201 (a derivative of pMLSV, previously described by Cosman et al., *Nature* 312: 768, 1984), SV40 and cytomegalovirus DNA and comprises, in sequence with the direction of transcription from the origin of replication: (1) SV40 sequences from coordinates 5171-270 including the origin of replication, enhancer sequences and early and late promoters; (2) cytomegalovirus sequences including the promoter and enhancer regions (nucleotides 671 to +63 from the sequence published by Boechart et al. (*Cell* 41:521, 1985); (3) adenovirus-2 sequences containing the first exon and part of the intron between the first and second exons of the tripartite leader, the second exon and part of the third exon of the tripartite leader and a multiple cloning site (MCS) containing sites for XhoI, KpnI, SmaI, NotI and BglI; (4) SV40 sequences from coordinates 4127-4100 and 2770-2533 that include the polyadenylation and termination signals for early transcription; (5) sequences derived from pBR322 and virus-associated sequences VAI and VAII of pDC201, with adenovirus sequences 10532–11156 containing the VAI and VAII genes, followed by pBR322 sequences from 4363-2486 and 1094-375 containing the ampicillin resistance gene and origin of replication.

The resulting WI-26VA4 cDNA library in pDC302 was used to transform *E. coli* strain DH5α, and recombinants were plated to provide approximately 1000 colonies per plate and sufficient plates to provide approximately 50,000 total colonies per screen. Colonies were scraped from each plate, pooled, and plasmid DNA prepared from each pool. The pooled DNA was then used to transfect a sub-confluent layer of monkey COS-7 cells using DEAE-dextran followed by chloroquine treatment, as described by Luthman et al. (*Nucl. Acids Res.* 11:1295, 1983) and McCutchan et al. (*J. Natl. Cancer Inst.* 41:351, 1986). The cells were then grown in culture for three days to permit transient expression of the inserted sequences. After three days, cell culture supernatants were discarded and the cell monolayers in each plate assayed for IL-7 binding as follows. Three ml of binding medium containing $5 \times 10^{-10}$ M $^{125}$I-IL-7 was added to each plate and the plates incubated at 25° C. for 90 minutes. This medium was then discarded, and each plate was washed once with cold binding medium (containing no labeled IL-7) and twice with cold PBS. The edges of each plate were then broken off, leaving a flat disk which was contacted with X-ray film for 72 hours at −70° C. using an intensifying screen. IL-7 binding activity was visualized on the exposed films as a dark focus against a relatively uniform background.

After approximately 100,000 recombinants from the library had been screened in this manner, one transfectant pool was observed to provide IL-7 binding foci which were clearly apparent against the background exposure.

A frozen stock of bacteria from the positive pool was then used to obtain plates of approximately 200 colonies. Replicas of these plates were made on nitrocellulose filters, and the plates were then scraped and plasmid DNA prepared and transfected as described above to identify a positive plate. Bacteria from individual colonies from the nitrocellulose replica of this plate were grown in 2 ml cultures, which were used to obtain plasmid DNA, which was transfected into COS-7 cells as described above. In this manner, a single clone, clone H1, was isolated which was capable of inducing expression of human IL-7R in COS cells. The cDNA insert was subcloned into the plasmid pGEMBL18, a derivative of the standard cloning vector pBR322 containing a polylinker having a unique EcoRI site, a BamHI site and numerous other unique restriction sites. An exemplary vector of this type is described by Dente et al. (*Nucl. Acids Res.* 11:1645, 1983). The cDNA coding region of clone H1 corresponds to the sequence of nucleotides 1–882 of FIGS. 2A–2C with the exception that clone H1 has an ATC codon encoding Ile$^{46}$ and a GTC codon encoding Val$^{118}$; clone H1 also has a nucleotide sequence of GTG AGT GTT TTT GGT GCT encoding an C-terminal amino acid sequence of Val Ser Val Phe Gly Ala. A bacterial stab of IL-7R cDNA clone H1 in the expression vector pDC302 has been deposited with the American Type Culture Collection, 12301 Parklawn Drive, Rockville, Md. 20852, USA, under the name pCAV/NOT-IL-7R, Accession Number 68014.

An additional human cDNA clone encoding IL-7R was isolated from a cDNA library constructed from reverse transcription of polyadenylated mRNA isolated from total RNA extracted from peripheral blood T lymphocytes (purified by E-rosetting) which had been activated for 18 hours with phytohemaglutinin and phorbol 12-myristate 13-acetate. Polyadenylated mRNA was isolated by chromatography on oligo-dT cellulose, and reverse transcribed using standard techniques to provide a first strand cDNA. This cDNA was rendered double-stranded using DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., *DNA Cloning: A Practical Approach*, Glover, ed., IRL Press, pp. 49–78). The ligated DNA was packaged into phage particles using a commercially available kit to generate a library of recombinants (Stratagene Cloning Systems, San Diego, Calif., USA.) Recombinants were plated on *E. coli* strain C600(hfl-) and screened by plaque hybridization techniques under conditions of high stringency (63°, 0.2 X SSC) using a $^{32}$P-labeled probe made from the human IL-7R cDNA clone H1. A hybridizing clone (clone H20) was identified which spans the entire coding region of IL-7R. FIGS. 2A–2C show the nucleotide sequence of the coding region of cDNA clone H20 and the corresponding amino acid sequence of a biologically active membrane-bound human IL-7R protein.

Example 3

Isolation of Soluble Human cDNA Clones Which Hybridize to Human IL-7 Receptor Probe DNAs and Encode Biologically Active Human IL-7R A $^{32}$P-labeled probe made from clone H1 was used to rescreen the WI-26 library and isolate a hybridizing clone (clone H6). Sequence analysis showed that clone H6 has the nucleotide sequence of FIGS. 3A–3B, which encodes a soluble IL-7 binding protein lacking a transmembrane region. Clone H6 is believed to be the result of an alternate mRNA splicing event in which the exon containing the transmembrane region (corresponding to nucleotides 729–822 of the full-length clone H20, shown in FIGS. 2A–2C) is deleted. Clone H6 thus encodes a secreted soluble form of the IL-7 receptor.

Example 4

Isolation of Murine cDNA Clones Which Hybridize to Human IL-7 Receptor Probe DNAs A $^{32}$P-labeled probe was prepared from the 2131 base pair (bp) fragment of clone H1 (see Example 2) by random priming using DNA polymerase I, as described by the manufacturer (Amersham, Arlington Heights, Ill., USA).

A cDNA library was constructed by reverse transcription of polyadenylated mRNA isolated from total RNA extracted from the cultured cells of the murine pre-B cell line 70Z/3 (ATCC Accession No. TIB 158). The cDNA was rendered double-stranded using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., *DNA Cloning: A Practical Approach*, Glover, ed., IRL Press, pp. 49–78). The ligated DNA was packaged into phage particles using a commercially available kit (Stratagene Cloning Systems, San Diego, Calif., USA 92121) to generate a library of recombinants. Recombinants were plated on *E. coli* strain C600(hfl⁻) and screened by standard plaque hybridization techniques under conditions of moderate stringency (50° C., 2 X SSC).

Two murine cDNA clones (clones P1 and P2) which hybridized to the human IL-7R probe were isolated from a screen of approximately 300,000 phage clones from the 70Z/3 cDNA library. The clones were plaque purified and used to prepare bacteriophage DNA which was digested with EcoRI, followed by preparative agarose gel electrophoresis, and then subcloned into EcoRI-cut pGEMBL. Clone P1 spans the entire coding region of the receptor protein, but contains an insert of 74 nucleotides in the 5' portion of the cDNA, due to an error in splicing, that would result in the premature termination of translation when expressed. Clone P2 codes for only the 5' portion of the cDNA. In order to obtain a full-length murine IL-7R cDNA, a hybrid cDNA molecule was constructed from clones P1 and P2 in the pDC302 expression vector described in Example 2. A 5' HindIII restriction fragment of cDNA clone P2 was ligated to a 3' restriction fragment of cDNA clone P1. The partial nucleotide sequence and predicted amino acid sequence of the coding region of the resulting hybrid cDNA is shown in FIGS. 4A–4C.

Example 5

Binding Characteristics of Human IL-7 Receptors

The various clones isolated or synthesized above were analyzed using the binding assays described in Example 1. Equilibrium binding experiments conducted with WI-26VA4 cells (1.33 x $10^7$ cells/ml) as described in Example 1B produced curvilinear Scatchard plots (Scatchard, *Ann. N.Y. Acad. Sci.* 51:660–672, 1949) as observed with the murine pre-B cell line IxN/2b (Park et al., J. Exp. Med. in press, 1990), showing both high ($K_a$=5.6±3.4 x $10^9$ M$^{-1}$) and low ($K_a$=9.7±3.5 x $10^7$ M$^{-1}$) binding affinities.

Human IL-7R was analyzed by transfecting COS cells with human IL-7R clone H20 as described in Example 1B. The data produced biphasic Scatchard plots similar to those observed for $^{125}$I-IL-7 binding to WI-26VA4 cells. From an average of two independent experiments, the COS cells expressing human IL-7R clone H20 had approximately 100,000 high affinity sites ($K_a$=3 x $10^9$ M$^{-1}$) and greater than 1 x $10^6$ low affinity sites ($K_a$=1 x $10^7$ M$^{-1}$) per cell. COS cells expressing human IL-7R clone H20 also produced a curvilinear Scatchard plot, showing the presence of two classes of IL-7 binding sites with apparent $K_a$ values of 4.6 x $10^9$ M$^{-1}$ and 4.1 x $10^7$ M$^{-1}$. Although the number of specific binding sites per cell varied between transfections, the data used to generate the above $K_a$ values indicated 3960 high affinity sites and 3.8 x $10^5$ total low affinity sites. These results demonstrate that the binding characteristics of recombinant human IL-7R expressed in COS-7 cells are very similar to those of the naturally occurring receptors found on WI-26VA4 cells.

The binding characteristics of the receptor molecule encoded by cDNA H6 was also analyzed. Clone H6 lacks the putative transmembrane domain and is secreted from COS-7 cells. Following transfection of this clone into COS-7 cells, no surface-bound receptors were detectable other than those naturally occurring on the COS-7 cells. Cell supernatant of the COS-7 cells was tested as described above in Example 1D to determine if binding of $^{125}$I-labeled IL-7 to the IL-7 receptors present on IxN/2b cells was inhibited. Preincubation of the $^{125}$I-labeled IL-7 with conditioned media from COS-7 cells transfected with cDNA H6 resulted in the subsequent inhibition of binding of $^{125}$I-IL-7 to IxN/2b cells. Media from COS-7 cells transfected with the plasmid pDC302 alone or from cells expressing the membrane-bound receptor encoded by cDNA H20 had little or no effect. Thus, the receptor protein coded for by cDNA H6, which lacks the transmembrane and C-terminal domains, is secreted and is capable of binding IL-7 in solution.

Example 6

Preparation of Monoclonal Antibodies to IL-7R

Preparations of purified recombinant IL-7R, for example, human IL-7R, or transfected COS cells expressing high levels of IL-7R are employed to generate monoclonal antibodies against IL-7R using conventional techniques, for example, those disclosed in U.S. Pat. No. 4,411,993. Such antibodies are likely to be useful in interfering with IL-7 binding to IL-7 receptors, for example, in ameliorating toxic or other undesired effects of IL-7, or as components of diagnostic or research assays for IL-7 or soluble IL-7 receptor.

To immunize mice, IL-7R immunogen is emulsified in complete Freund's adjuvant and injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with IL-7R, for example, by adaptations of the techniques disclosed by Engvall et al., *Immunochem.* 8:871 (1971) and in U.S. Pat. No. 4,703,004. Positive clones are then injected into the peritoneal cavities of syngeneic Balb/c mice to produce ascites containing high concentrations (>1 mg/ml) of anti-IL-7R monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

We claim:

1. An antibody that selectively binds an interleukin-7 receptor, wherein said interleukin-7 receptor comprises an amino acid sequence selected from the group consisting of amino acids 1 to 439 of FIGS. 2A–2C, amino acids 1 to 242 of FIGS. 3A–3B, and amino acids 1 to 439 of FIGS. 4A–4C.

2. An antibody according to claim 1, wherein said antibody is a monoclonal antibody.

3. A monoclonal antibody according to claim 2, wherein said interleukin-7 receptor is a human interleukin-7 receptor having the amino acid sequence consisting of the amino acids 1 to 439 of FIGS. 2A–2C.

4. A monoclonal antibody that selectively binds a human interleukin-7 receptor wherein said interleukin-7 receptor is a soluble human interleukin-7 receptor having the amino acid sequence consisting of the amino acids 1–219 of FIGS. 2a–2B.

5. A hybridoma cell line that produces a monoclonal antibody according to claim 2.

6. A hybridoma cell line that produces a monoclonal antibody according to claim 4.

* * * * *